United States Patent
Johnson et al.

(10) Patent No.: US 7,114,501 B2
(45) Date of Patent: Oct. 3, 2006

(54) TRANSVERSE CAVITY DEVICE AND METHOD

(75) Inventors: Wesley Johnson, Eden Praire, MN (US); Deb Barber, Shakopee, MN (US); Thomas Hektner, Medina, MN (US); Larry Fuller, Woodbury, MN (US); Lawrence W. Wales, Maplewood, MN (US)

(73) Assignee: Spine Wave, Inc., Shelton, CT (US)

( * ) Notice: Subject to any disclaimer, the term of this patent is extended or adjusted under 35 U.S.C. 154(b) by 509 days.

(21) Appl. No.: 09/873,699

(22) Filed: Jun. 4, 2001

(65) Prior Publication Data

US 2002/0022856 A1 Feb. 21, 2002

Related U.S. Application Data

(60) Provisional application No. 60/227,050, filed on Aug. 21, 2000, provisional application No. 60/225,191, filed on Aug. 14, 2000.

(51) Int. Cl.
*A61B 17/00* (2006.01)

(52) U.S. Cl. .................... 128/877; 601/61; 601/79; 601/86

(58) Field of Classification Search .............. 128/887; 606/60–61, 79–96
See application file for complete search history.

(56) References Cited

U.S. PATENT DOCUMENTS

| | | | |
|---|---|---|---|
| 3,030,951 A | 4/1962 | Mandarino | |
| 4,204,531 A | 5/1980 | Aginsky | |
| 4,262,676 A | 4/1981 | Jamshidi | |
| 4,542,741 A * | 9/1985 | Burgin ................ | 128/303.1 |
| 4,554,914 A | 11/1985 | Kapp et al. | |
| 5,013,318 A | 5/1991 | Spranza, III | |
| 5,108,404 A * | 4/1992 | Scholten et al. ........... | 606/94 |
| 5,147,364 A * | 9/1992 | Comparetto ............. | 606/85 |
| 5,171,248 A | 12/1992 | Ellis | |
| 5,403,318 A * | 4/1995 | Boehringer ............... | 606/82 |
| 5,415,660 A | 5/1995 | Campbell et al. | |
| 5,423,824 A | 6/1995 | Akerfeldt et al. | |
| 5,431,671 A * | 7/1995 | Nallakrishnan ........... | 606/167 |
| 5,445,639 A | 8/1995 | Kuslich et al. | |
| 5,468,245 A | 11/1995 | Vargas, III | |
| 5,505,733 A | 4/1996 | Justin et al. | |
| 5,505,738 A | 4/1996 | Hempel et al. | |
| 5,522,398 A | 6/1996 | Goldenberg et al. | |
| 5,591,170 A | 1/1997 | Spievack et al. | |
| 5,632,746 A * | 5/1997 | Middleman et al. ........ | 606/78 |
| 5,695,513 A | 12/1997 | Johnson et al. | |
| 5,746,771 A * | 5/1998 | Clement et al. .......... | 623/23.22 |
| 5,827,328 A | 10/1998 | Buttermann | |
| 5,846,244 A * | 12/1998 | Cripe ...................... | 606/82 |
| 5,928,239 A * | 7/1999 | Mirza ...................... | 606/79 |
| 5,980,526 A * | 11/1999 | Johnson et al. ........... | 606/86 |
| 6,068,642 A | 5/2000 | Johnson et al. | |
| 6,127,597 A | 10/2000 | Beyar et al. | |
| 6,127,697 A | 10/2000 | Beyar et al. | |

(Continued)

FOREIGN PATENT DOCUMENTS

WO WO 97/31577 9/1997

(Continued)

*Primary Examiner*—Michael A. Brown
(74) *Attorney, Agent, or Firm*—Maginot, Moore & Beck

(57) ABSTRACT

The invention teaches the use of a surgical instrument for creating and preparing a cavity in a bony intervertebral body. Asymmetrical cutting structures selectively open a cavity which has a relatively large surface area in the vertical direction.

13 Claims, 7 Drawing Sheets

U.S. PATENT DOCUMENTS 6,383,188 B1 5/2002 Kuslich et al.
6,440,138 B1 8/2002 Reiley et al.
6,575,978 B1 6/2003 Peterson et al.
6,676,665 B1 1/2004 Foley et al.

FOREIGN PATENT DOCUMENTS

| WO | WO99/00074 | 1/1999 |
|----|------------|--------|
| WO | WO99/25253 | 5/1999 |
| WO | WO99/252453 | 5/1999 |
| WO | WO99/34737 | 7/1999 |
| WO | WO99/56675 | 11/1999 |

\* cited by examiner

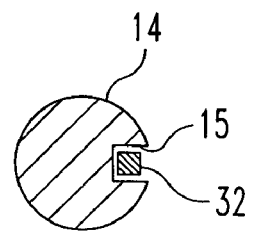
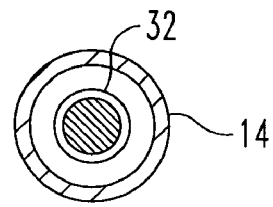
Fig. 4    Fig. 5
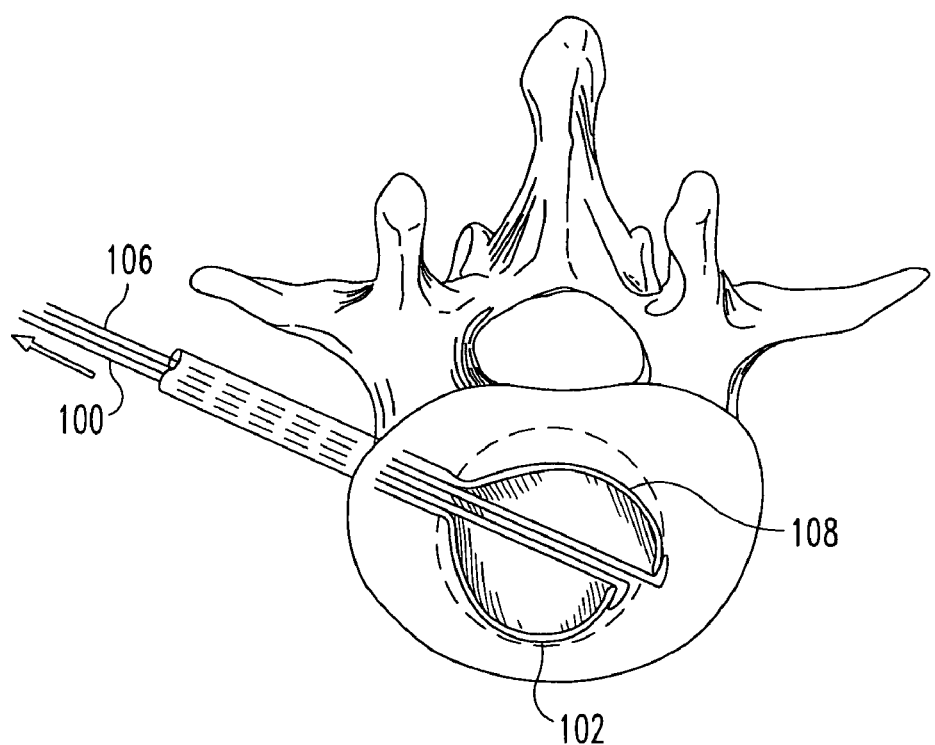
Fig. 6

TRANSVERSE CAVITY DEVICE AND METHOD

CROSS-REFERENCE TO RELATED CASES

The present case claims the benefit of, and incorporates by reference the following U.S. provisional applications:

U.S. Provisional Patent Application Ser. No. 60/227,050 filed Aug. 21, 2000, entitled "Vertebroplasty Cavity Creation using an Expanding Tube" and, U.S. Provisional Patent Application Ser. No. 60/225,191 filed Aug. 14, 2000, entitled "Vertebral Body Expander."

FIELD OF THE INVENTION

The present invention relates generally to the treatment of compression fractures in bones, and more specifically to a device and a method for cutting a "transverse" cavity in the bone as one part of a therapy.

BACKGROUND OF THE INVENTION

The human spine consists of a complex set of interrelated anatomic elements including a set of bones called vertebral bodies. Intervertebral discs separate most vertebral bodies. These discs includes a "spongy" nucleus pulpous surrounded by an annulus fibrosis "membrane." The annulus fibrosis connects the opposed endplates of adjacent vertebral bodies. All of these structures together with muscles act to provide motion, stability and protection for the spinal cord. When healthy, these structures effectively protect the spinal cord and allow for normal motion.

However, there are many disease states and aging processes that impact the patient. Osteoporosis and metastatic disease reduce the structural integrity of the vertebral bodies, predisposing them to fracture. Vertebral fractures can lead to loss of vertebral height, which can exacerbate existing neurological conditions or predispose the spine to other symptoms. Back pain often results from these conditions.

Vertebroplasty is an effort to stabilize these fractures and to alleviate this source of pain. Generally, if not treated, fractures and loss of height result in a cascade of injury which is undesirable. For this reason, various efforts have been directed at stabilizing and restoring the natural vertebral bodies of the back.

Many surgeon experts suggest that it is desirable to intervene and restore the height of the vertebral body and natural biomechanics of the spine, in addition to stabilizing the spine to provide pain relief. As an initial step to fracture reduction, which for vertebral compression fractures restores anatomic vertebral height, it may be desirable to cut a cavity that is approximately transverse to the vertical axis of the vertebral body. This cavity is intended to create a large, uniform, initial surface area for fracture reduction devices. The transverse cavity reduces contact stress in supporting bone and decreases the likelihood of cancellous compaction associated with prior art techniques. Thus, this step increases the likelihood that the fracture will be reduced rather than simply creating a large cavity within a bony structure. In general, it may be desirable to locate this transverse cavity near the fracture, which is generally located in the anterior portion of the vertebral body. It is important to create a shallow cavity at the correct location to minimize disruption of cancellous bone and to facilitate further therapeutic intervention.

The presently available techniques and devices expand along a path of least resistance within the cancellous bone. As a result, these devices do not expand in a predictable manner, often expanding vertically before expanding horizontally (transverse). Rather than consistently reducing the fracture, these techniques often crush the cancellous bone, creating an expanded cavity without necessarily reducing the fracture or restoring the natural anatomy.

Another reason for creating a narrow cavity is to impart known fracture zones in the bone. These fracture zones enable controlled movement of the bone during other therapeutic procedures. These fracture zones also create flow channels for various injectable materials that may be used in a further therapeutic intervention.

SUMMARY

In contrast to the prior art, the devices and methods of the present invention are used to create an initial cavity in the vertebral body that has a controlled shape and location. FIG. 13 represents a prior art procedure where a narrow and small cavity 17 is filled with a balloon and the overall "footprint" is small so that the total distraction force is also small. FIG. 14 represents a cavity created according to the invention filled with a balloon to apply distraction force. In this figure, the increased area of the "footprint" of the transverse cavity 18 permits greater distraction force per unit balloon pressure.

The vertebral body is entered through either a transpedicular or extrapedicular location with a needle, trocar or other access devices. The cavity creation tool of the invention is inserted into the cancerous bone of the vertebral body through the relatively small area aperture created by the trocar or needle. The cavity creation tool is then activated and manipulated.

In general, the tool is directed to a site near the bone fracture. In the context of a vertebral compression fracture, the fracture is typically located in the anterior portion of the vertebral body. Once positioned at the desired site, the device is used to create a cavity. Although several related embodiments of the cavity creation tool are contemplated and illustrated, each of them defines a cutting or shearing plane. Each device limits its action to a controlled area of the bone. The controlled area both defines and is a portion of the "transverse" cavity.

Once the preferred transverse cavity is created, any number of interventions can be performed. For example, a device that "expands" may be introduced to reduce the fracture. Typically, the reduction is intended to restore the normal anatomy. This expansion device may be removed or permanently implanted.

Once a fracture is reduced, the bone cavity may be filled with a bone filler material such as bone cement, allograft, or synthetic bone substitutes. The filler acts to increase the stability and strength of the bone. In some interventions, the filler may be combined with bone growth factors (BMPs, cell therapy, autologous growth factors) to accelerate bone remolding and increase the amount of bone remodeling. Likewise, other drugs or therapies (including but not limited to antibiotics, chemotherapy, and other drug therapies) may be combined with the bone filler.

Although the invention is illustrated within the vertebral body compression fracture treatment context, other secondary interventions or operations can be contemplated for using the shaped cavity.

Although the invention is particularly useful for the treatment of vertebral bodies, it should be understood that similar bone fracture geometries exist in other parts of the body. For this reason, the devices and methods of the invention may be used in the treatment of any compaction fracture, such as but not limited to the tibial plateau fractures, distal radius fractures, calcaneous, distal tibial fractures, and humeral fractures.

BRIEF DESCRIPTION OF THE DRAWINGS

Illustrative embodiments of the inventions are shown throughout the several views of the drawings. For ease of illustration, the inventions are disclosed in the context of the repair of a vertebral body, however the device and method can be applied in other compression fracture applications including, but not limited to tibial plateau, distal radius, calcaneous, distal tibial fractures, and humeral fractures.

In these illustrative but not limiting drawings, like reference numerals indicate equivalent structure, wherein:

FIG. 4 is a cross section of a portion of a cavity creation tool;

FIG. 5 is a cross section of a portion of a cavity creation tool;

FIG. 6 is a cross section of a vertebral body illustrating a portion of a cavity creation tool;

DETAILED DESCRIPTION

Figure 1:
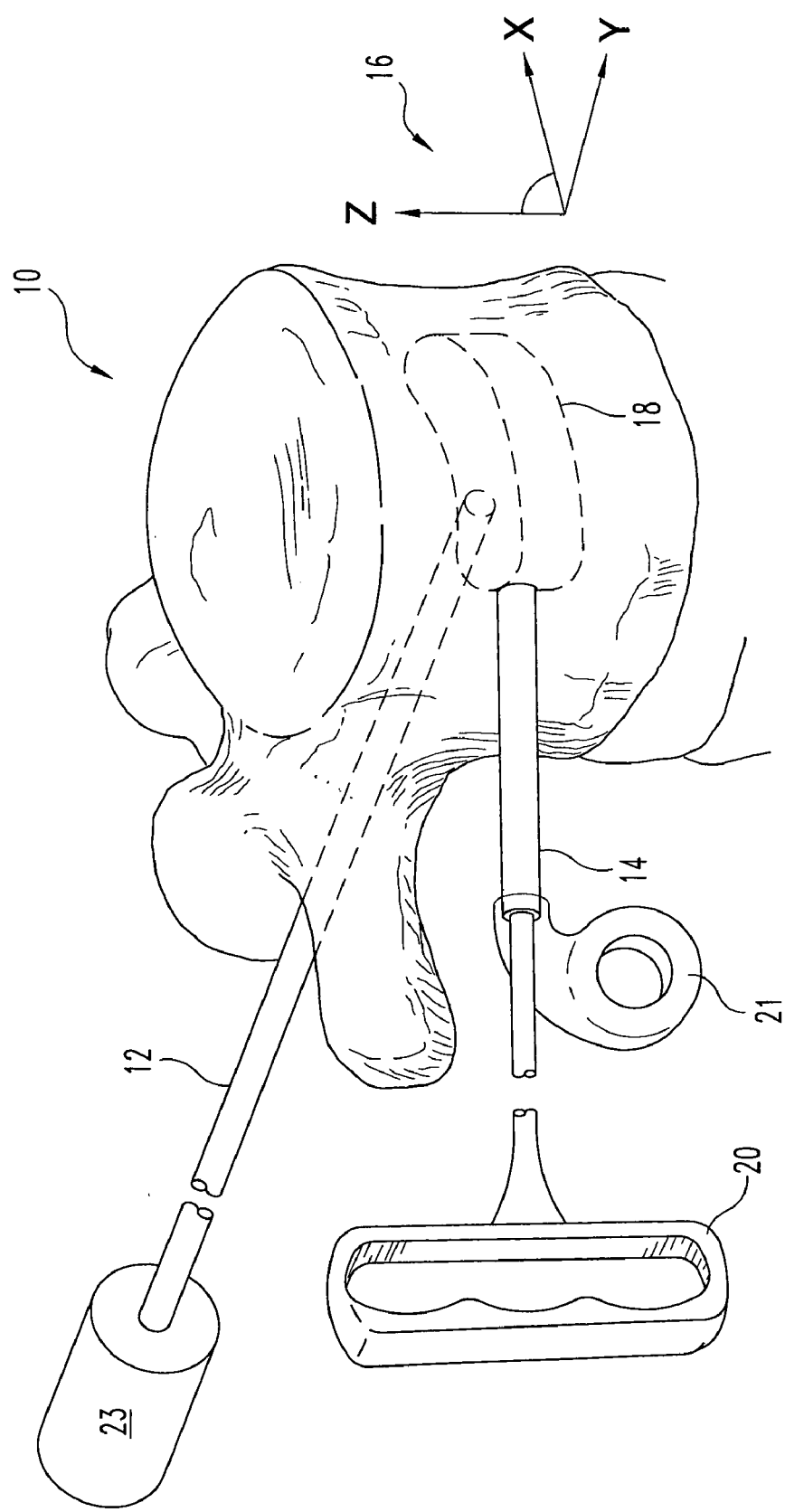
FIG. 1 is a phantom view of a vertebral body showing a transverse cavity, certain tool features and a coordinate system.

FIG. 1 is a phantom view of a vertebral body showing a transverse cavity 18 and a coordinate system 16. This figure shows a vertebral body 10 in isolation. Two possible surgical entry points into the vertebral body contemplated within the scope of the invention are illustrated. One entry point is "transpedicular." This approach is indicated by the physical location of tube 12, traveling through the pedicle into the vertebral body 10. Another approach is "extra-pedicular." This access approach is illustrated by tool 14 entering the vertebral body at a location lateral of the transpedicular approach on the posterolateral corner of the vertebral body.

The typical surgery will include a small incision in the back adjacent to the vertebral body. Next, a small gauge needle or guide-wire is introduced to confirm proper positioning under fluoroscopy. Physicians typically utilize an 11-gauge needle for the transpedicular approach and a larger needle or tube (up to 6 mm ID) for the extra-pedicular approach. Many physicians advance cannulated tools over a small gauge needle to successively increase the size of the working channel.

Other physicians may prefer to place a guide catheter at the site and to introduce tools though the lumen of the guide catheter. In general, the tools described herein can be used either over the wire or through a guide catheter or alone at the election of the physician.

In this figure, a coordinate system 16 identifies a vertical direction Z, which points along the spine. The Y-direction is generally anterior. It is the purpose of the invention to create a cavity with a fixed and controlled vertical extent (Z-axis height) and a controlled shape in the X-Y plane. For the purposes of this disclosure, the term transverse cavity will be used interchangeably with a cavity created parallel to the surface that is to be reduced or restored to its normal anatomic position, and generally normal to the force applied. The surface that is reduced or displaced defines the X-Y plane. This definition holds for other procedures performed with the invention.

Returning to the figure, the cavity 18 is typically ovaloid in shape as projected in the X-Y plane. The ovaloid shape has an approximately uniform height in the Z direction. This "shape" is referred to throughout the specification as a "transverse cavity" for the vertebral body application illustrated in these figures. Therefore the X-Y plane is defined as the "transverse plane" and the Z-axis direction may be referred to as the "vertical axis." It is a characteristic of all the embodiments of the tools shown in the application that the cross sectional area of the tool at the entry point into the bone is smaller than the transverse cavity created with the tool.

To facilitate description of the invention, the distal "working" structures of the cavity creation tools are illustrated in isolation while the proximal manipulation handles as contemplated are shown generically as handle 20 and finger loop 21. In each embodiment, a handle structure 20 can be moved with respect to the tool sheath or tool body 14. In each embodiment, the relative motion between handle 20 and sheath 14 activates the distal working surfaces of the device. The handle 20 or the finger loop 21 is indexed to the distal working surfaces to provide confirmation of the orientation of the working surfaces with respect to the bone structures.

It is contemplated that in addition to direct manual manipulation, other power sources can be used to actuate the working surfaces, including hydraulic or pneumatic cylinders and electromechanical actuators shown generically in FIG. 1 as power source 23. In general, purely manual mechanical mechanisms are preferred because they improve tactile feedback to the physician.

The tools may be made of conventional materials, with stainless steel preferred for "blade" embodiments and Nitinol or other super elastic alloys adopted for the flexible arm embodiments. The tools may be reusable or disposable. Materials choices do not appear critical for carrying out the invention.

The overall length of the cavity creation tool from the handle structures 20 and 21 to the working distal tip may vary to facilitate the particular surgical procedure. For example, a length of 220 cm is useful for the vertebral application, while a length of 60 cm is a practical value for a tibial plateau procedure.

Figure 2:
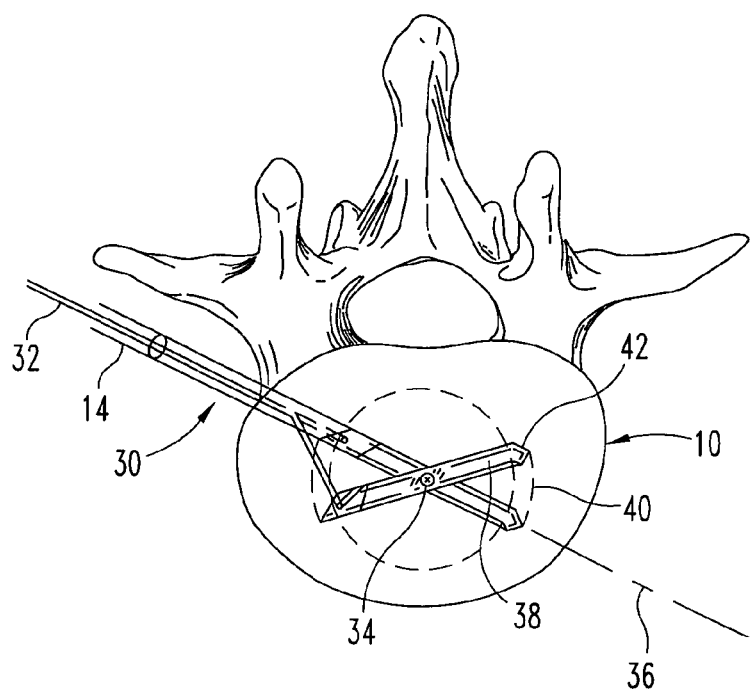
FIG. 2 is a cross section of a vertebral body illustrating a portion of a cavity creation tool.

FIG. 2 shows an embodiment of the cavity creation tool 30 that includes a blade 38 mounted on the tool body 14 for rotational motion around the pivot 34. The rod 32 is coupled to a proximal handle 20 (FIG. 1) and a push-pull motion between the handle and the finger loop 21 (FIG. 1) causes the blade to sweep out an arc 40. The blade may be blunt or it may include a cutting surface 42. In operation, the blade 38 laterally loads cancellous bone, breaking or cutting the bone in the X-Y plane of the cavity. The pivot and blade are confined to a transverse plane so this action creates the transverse cavity. By advancing the tool along the axis 36, the cavity may take an approximately oval shape in the X-Y plane.

Figure 3:
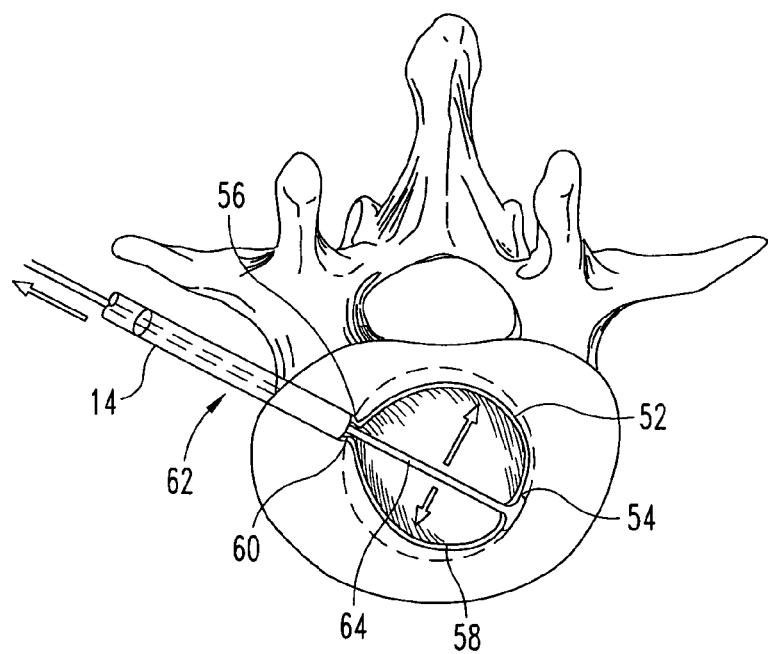
FIG. 3 is a cross section of a vertebral body illustrating a portion of a cavity creation tool.

FIG. 3 shows a cavity creation tool 62 having a distal end that is positioned in a vertebral body. The distal end includes two arms. A first arm 52 is anchored to the tube 14 with a hinge point mechanism 56 at a first end. The second end of the arm 52 is coupled to the pull rod 64. Relative motion between the tube 14 and the pull rod 64 expands the first arm in a transverse plane. This particular embodiment of the tool is asymmetric and the tool includes a second arm 58 that is anchored to the tube 14 with a hinge mechanism 60. The first and second arms define a plane for the operation of the device in the transverse plane.

FIG. 4 shows a cross section of the tool body 14 having a notch or groove 15 for locating and restraining a pull rod 32. The tool body cross section defines the tool body area for the cavity creation tool. In general, the tool may be inserted into a bone through a hole of the size of the tool body area. This parameter or area is always smaller than the "footprint" of the transverse cavity in the X-Y plane. The cross section of this portion of the tool defines the tool body area.

FIG. 5 shows a pull rod 32 is constrained in a groove in the tool body 14. In this embodiment the pull rod actuates a blade or other structure. The cross section of this portion of the tool defines the tool body area.

FIG. 6 shows an embodiment of the tool that has two pull or push rods 100 and 106. Pull rod 106 operates a first arm 108 while the second arm 102 is activated by the independent pull rod 102. The asymmetrical operation of the two independent arms can be used to control the shape of the cavity by directing expansion of the cavity to preferred areas within the vertebral body.

Figure 7:
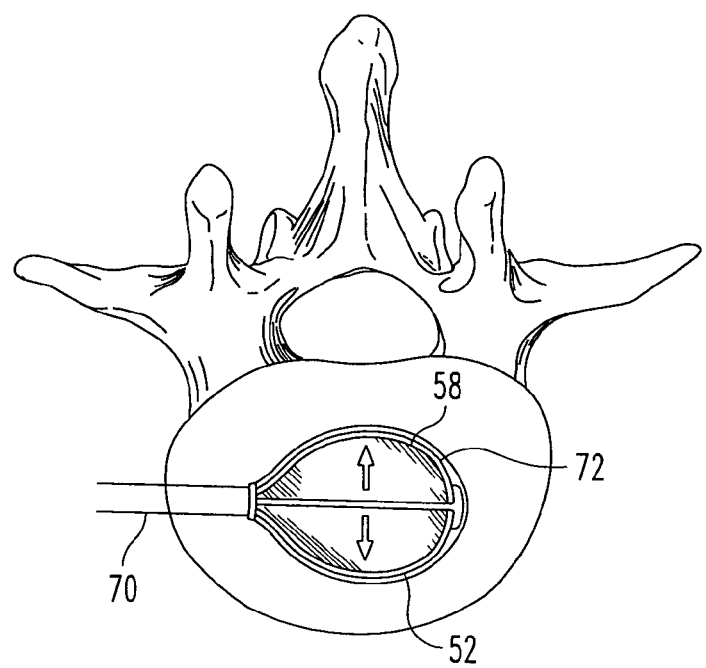
FIG. 7 is a cross section of a vertebral body illustrating a portion of a cavity creation tool.

FIG. 7 shows an embodiment of the tool 70 where a container 72 surrounds a pair of arms 52 and 58. The container interacts with the cancellous bone as the pull rod activates the arms and moves them against the cancellous bone. The container prevents debris from interfering with the retraction of the arms. The container 72 can be subsequently inflated to reduce the fracture and restore the natural anatomy. Finally, the container may be detached and left behind.

In this particular embodiment, the first and second arms are identical, and will normally create a symmetric cavity. The container 72 is optional and the arms can be used alone in a fashion analogous to other versions of the tool.

In this particular embodiment, the first and second arms have blunt dissection surfaces on the exterior of the arms to interact with cancellous bone. In this embodiment, the first and second arms may also have different mechanical properties for the creation of an asymmetric cavity.

Figure 8:
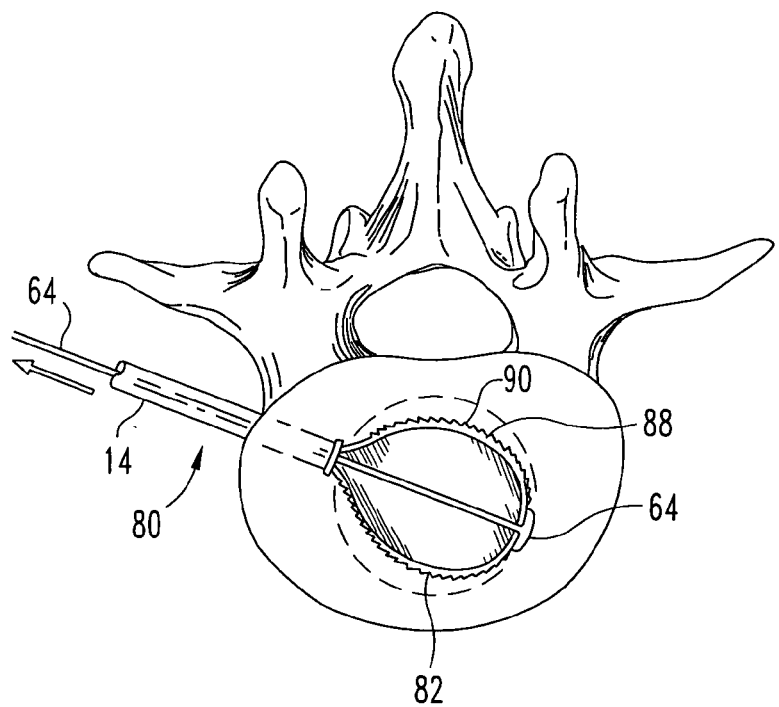
FIG. 8 is a cross section of a vertebral body illustrating a portion of a cavity creation tool.

FIG. 8 shows an embodiment of the cavity creation tool 80 that includes saw-like teeth on the first arm 88 and the second arm 82. Once again, traction on the pull rod 64 causes the teeth on the arms to cut through the cancellous bone. In a fashion similar to related embodiments, the arms lie in and define a cutting plane that creates a transverse cavity. The saw teeth typified by tooth 90 can be moved by manipulating both the pull rod and the tube.

Figure 9:
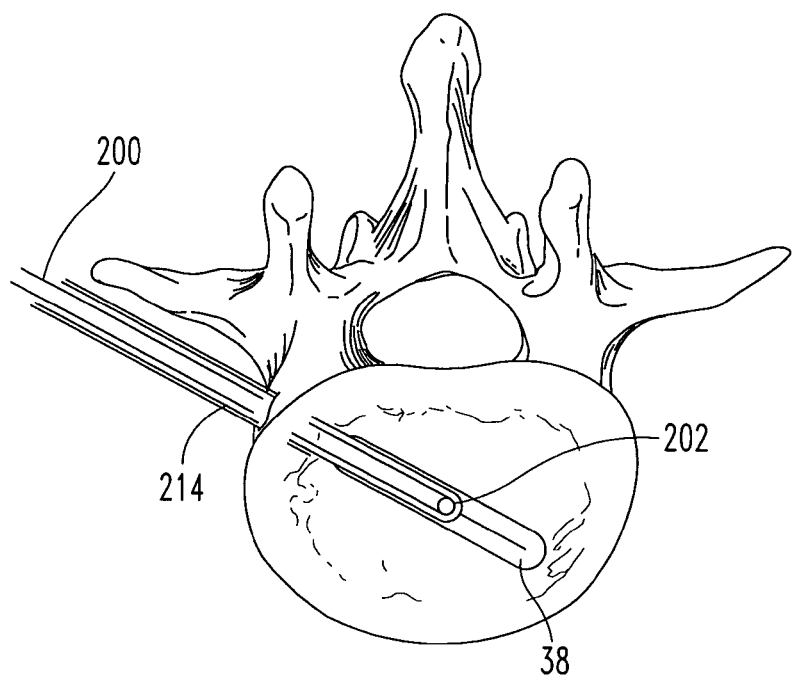
FIG. 9 is a cross section of a vertebral body illustrating a portion of a cavity creation tool.

FIG. 9 shows a cable-actuated device with a cable 200 wrapping a spindle or axle 202 mounted on the tool body 214. Cable motion results in sweeping out an arc 210 as seen in FIG. 10.

Figure 10:
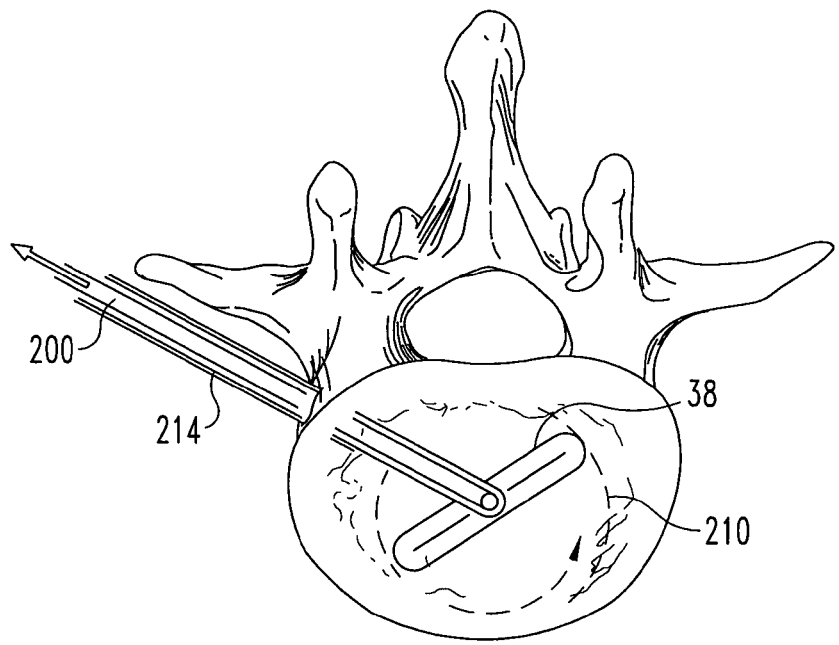
FIG. 10 is a cross section of a vertebral body illustrating a portion of a cavity creation tool.

FIG. 10 shows the blade 38 can sweep through 360 degrees because of cable actuation. An arc of less than 360 degrees may be used when a non-circular cavity is required.

Figure 11:
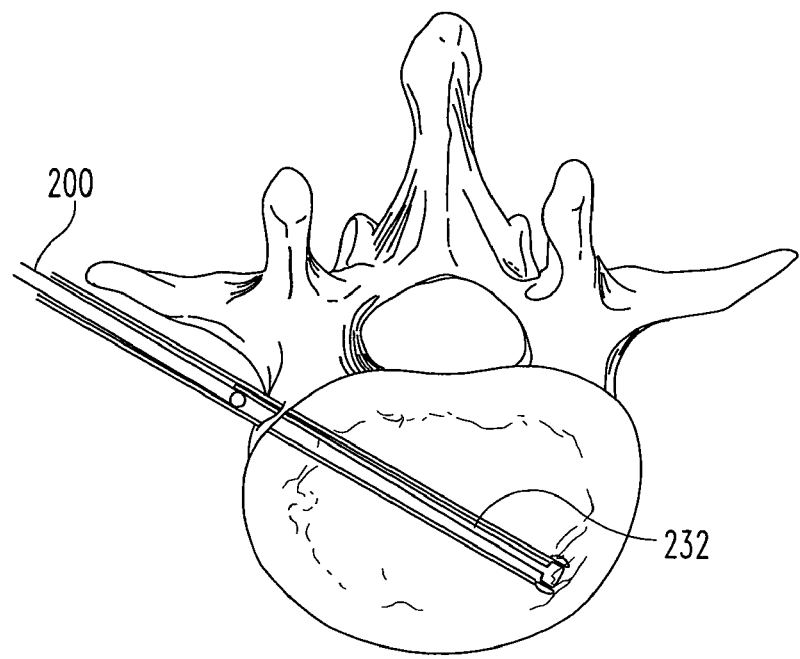
FIG. 11 is a cross section of a vertebral body illustrating a portion of a cavity creation tool.

FIG. 11 is a cable-operated version with the pull rod 232 coupled to cable 200. In this device, the pull on the cable forces the flex arms 202 and 208 in an outward direction to form the transverse cavity.

Figure 12:
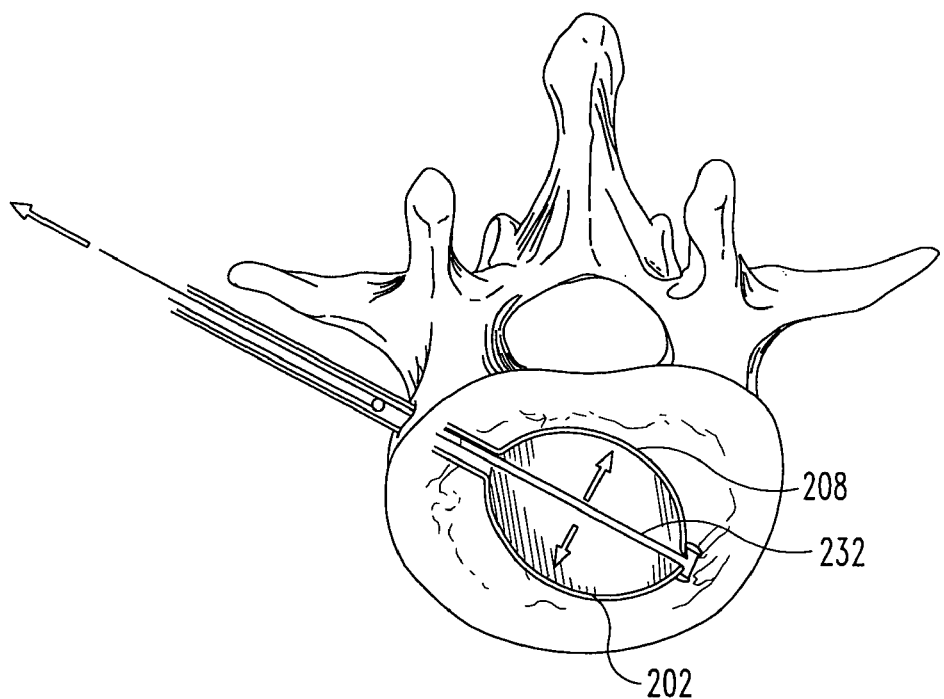
FIG. 12 is a cross section of a vertebral body illustrating a portion of a cavity creation tool.

FIG. 12 shows the cable-operated version of FIG. 9 with the arms deployed, creating a transverse cavity.

Figure 13:
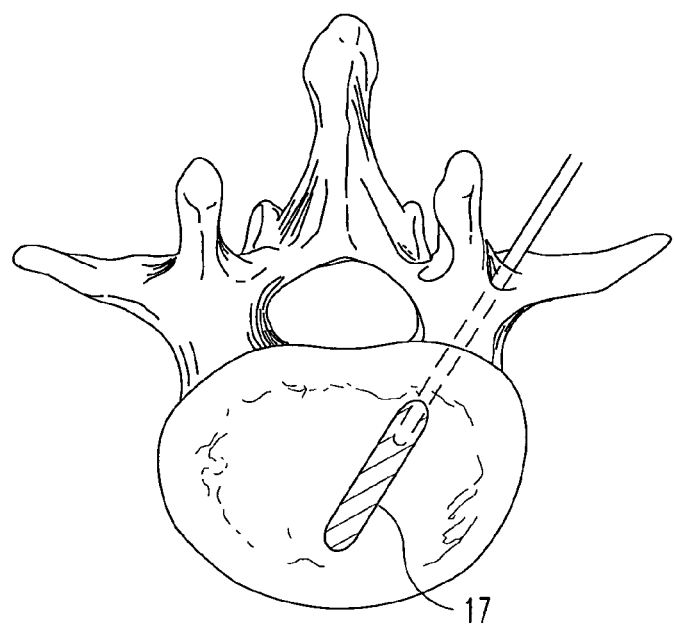
FIG. 13 is a cross section of a vertebral body illustrating a portion of a hydraulic lifting device of the Prior Art; and, FIG. 14 is a cross section of a vertebral body illustrating a portion of a hydraulic lifting device.

FIG. 13 which represents the prior art is a schematic of a balloon or other hydraulic lifting device as it is initially inserted into the vertebral body.

Figure 14:
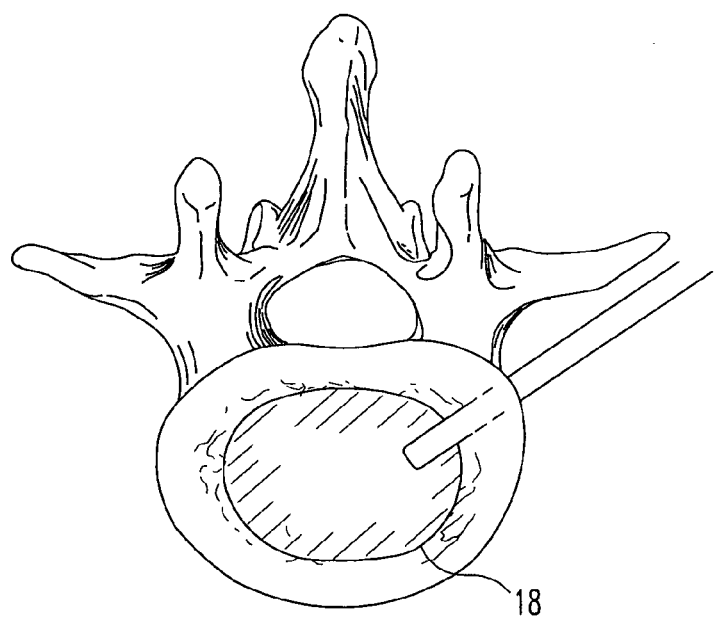

FIG. 14 is a schematic of the increased lifting force generated by a balloon or other hydraulic lifting device which immediately reaches a broad surface area because of the transverse cavity that has been prepared before deploying the balloon or hydraulic lifting device.

Although the invention has been illustrated in one context, it should be apparent that the device features maybe modified or combined in alternate configurations.

What is claimed is:

1. A method of creating a transverse cavity in a bone having a compression fracture, comprising the steps of:
   identifying a surface in a bone that is to be restored to its normal anatomical position, said surface generally defining a transverse plane;
   inserting a tool having a tool body area into the bone adjacent said surface;
   after insertion, activating a movable element operably supported by said tool in a direction outwardly from said tool body and through a path consisting essentially of a substantially flat plane that is substantially parallel to said surface to define a transverse cavity having an area greater than said tool body area and a substantially uniform height in a direction generally perpendicular to said transverse plane.

2. The method of claim 1 wherein said movable element includes a blade pivotably mounted on said tool body to swing through an arc.

3. The method of claim 2, wherein said blade is blunt.

4. The method of claim 2, wherein said blade includes a cutting surface.

5. The method of claim 2, wherein said blade is mounted on said tool body for rotational motion about a pivot.

6. The method of claim 5, wherein said rotational motion of said blade is activated by a push-pull motion.

7. The method of claim 2, wherein said blade is defined by a flexible element pivotally mounted to said tool body at a hinge point, said flexible element swinging outwardly upon being activated to define said transverse cavity.

8. The method of claim 1, wherein said area of said transverse cavity is generally oval in shape.

9. The method of claim 1, wherein the compression fracture to be restored is selected from the group consisting of vertebral compression fractures, tibial plateau fractures, distal radius fractures, calcareous fractures, distal tibial fractures, and humeral fractures.

10. The method of claim 1, wherein the compression fracture is a vertebral compression fracture and said surface to be restored is an endplate surface of a vertebral body.

11. The method of claim 10, wherein said tool is inserted through the pedicle of said vertebral body along a surgical entry point.

12. The method of claim 11, wherein said surgical entry point is selected from the group of approaches consisting of a transpedicular approach and an extra-pedicular approach.

13. The method of claim 1, wherein said tool body is generally elongate defining a longitudinal axis and while said movable element is activated said tool body is maintained in a fixed position relative to any rotational movement about said longitudinal axis.

* * * * *

UNITED STATES PATENT AND TRADEMARK OFFICE
CERTIFICATE OF CORRECTION

| | | |
|---|---|---|
| PATENT NO. | : 7,114,501 B2 | Page 1 of 1 |
| APPLICATION NO. | : 09/873699 | |
| DATED | : October 3, 2006 | |
| INVENTOR(S) | : Johnson et al. | |

It is certified that error appears in the above-identified patent and that said Letters Patent is hereby corrected as shown below:

Col. 2, line 30: replace "cancerous" with -- cancellous --

Signed and Sealed this

Ninth Day of January, 2007

JON W. DUDAS
*Director of the United States Patent and Trademark Office*